United States Patent

Diaz

Patent Number: 5,807,350
Date of Patent: Sep. 15, 1998

[54] KINK RESISTANT CATHETER SHEATH INTRODUCER

[75] Inventor: Roberto Diaz, Miami, Fla.

[73] Assignee: Cordis Corporation, Miami, Fla.

[21] Appl. No.: 552,894

[22] Filed: Nov. 3, 1995

[51] Int. Cl.⁶ ................................................. A61M 5/00
[52] U.S. Cl. ........................................ 604/256; 604/167
[58] Field of Search .................... 604/264, 280, 604/28, 256, 246, 156, 158, 164, 167, 169; 128/656–658

[56] References Cited

U.S. PATENT DOCUMENTS

| | | | |
|---|---|---|---|
| 4,758,221 | 7/1988 | Jureidini | 604/95 |
| 4,787,882 | 11/1988 | Claren | 604/4 |
| 4,798,594 | 1/1989 | Hillstead . | |
| 4,895,565 | 1/1990 | Hillstead . | |
| 4,960,412 | 10/1990 | Fink | 604/167 |
| 5,125,903 | 6/1992 | McLaughlin et al. | 604/167 |
| 5,376,077 | 12/1994 | Gomringer | 604/167 |
| 5,417,665 | 5/1995 | De La Mata et al. . | |
| 5,453,095 | 9/1995 | Davila et al. . | |
| 5,466,230 | 11/1995 | Davilia | 604/256 |
| 5,558,652 | 9/1996 | Henke | 604/280 |

Primary Examiner—Michael Buiz
Assistant Examiner—Deborah B. Blyveis
Attorney, Agent, or Firm—Dean Garner

[57] ABSTRACT

A catheter or catheter sheath introducer, for insertion into a vessel of a patient. The catheter has a rigid housing at its proximal end. The housing has an annular valve for access to the lumen of catheter. The catheter further includes a flexible tube for insertion into the patient. Lastly, the catheter has a resilient transition member intermediate and separating the housing and the tube. The member has a greater flexibility than the tube such that if the catheter is bent, after it is inserted into the patient, it will bend along the transition member where there is no substantial reduction of the cross-sectional area of the lumen adjacent the bend.

9 Claims, 2 Drawing Sheets

KINK RESISTANT CATHETER SHEATH INTRODUCER

BACKGROUND OF THE INVENTION

Catheters, cannulas, or catheter sheath introducers, having hemostasis valves which are mounted on a housing on the end of a catheter are well known in the art. An example of a catheter sheath introducer is given in commonly assigned U.S. Pat. No. 4,895,565 issued to Hillstead on Jan. 23, 1990. The catheters have a distal end for insertion into the patient and a proximal end which remains external of the patient. Such catheters are used to facilitate the introduction of other catheters and guidewires into the vascular system of a patient, while minimizing injury to the patient at the access site. For some procedures, such as percutaneous transluminal angioplasty, one or more catheters are inserted into and removed from the patient repeatedly. The presence of the catheter sheath introducer causes the trauma to the body to be limited to only one catheter entering at the body access site. All other catheters and guidewires pass through the catheter introducer, and thus are not traumatic to the body at the access site.

Catheter sheath introducers typically have a hemostasis valve located within a housing at the proximal end. The valve can be made from a slit elastomeric partition or membrane. The valve is designed to seal against leakage of blood, as catheters and guidewires of varying diameters are passed therethrough.

The catheter introducer is usually inserted into the femoral or brachial artery of a patient. After it is inserted into the vessel, the catheter lies flat against the patient with its longitudinal axis substantially parallel to the ground. With this orientation the valve on the catheter is perpendicular to the eyesight of the physician, who is typically standing over the patient. In order to introduce a catheter or guidewire into the patient, the doctor will often bend the catheter introducer so that the valve is facing up, towards himself. This makes it easier for the physician to see the valve and insert a catheter or guidewire. After he has inserted a catheter or guidewire a small distance, he will stop bending the catheter introducer.

This bending of the catheter introducer, causes the flexible catheter tubing on the introducer to kink at or near its connection point to the rigid housing. After the physician stops bending the catheter introducer the tubing often remains kinked, which reduces the inside diameter of the tube at this point. This causes difficulty in introducing catheters or guidewires through the tubing.

There has, therefore, been a desire to produce a catheter sheath introducer which will resist or reduce kinking when it is bent after introduction into the patient such that the inside of the diameter of the catheter near the bend is not substantially reduced. There has also been a desire to produce such a catheter which is resilient and will return to its original orientation after it has been bent.

SUMMARY OF THE INVENTION

A catheter, or catheter sheath introducer, for insertion into a vessel of a patient. The catheter has a rigid housing at its proximal end. The housing has an annular valve for access to the lumen of catheter. The catheter further includes a flexible tube for insertion into the patient. Lastly, the catheter has a resilient transition member intermediate and separating the housing and the tube. The member has a greater flexibility than the tube such that if the catheter is bent, after it is inserted into the patient, it will bend along the transition member where there is no subtantial reduction of the cross-sectional area of the lumen adjacent the bend.

BRIEF DESCRIPTION OF THE DRAWINGS

While the specification concludes with claims which particularly point out and distinctly claim the subject matter forming the present invention, it is believed that the invention will be better understood from the following description of the preferred embodiment taken in conjunction with the accompanying drawings wherein:

DETAILED DESCRIPTION OF THE INVENTION

Figure 1:
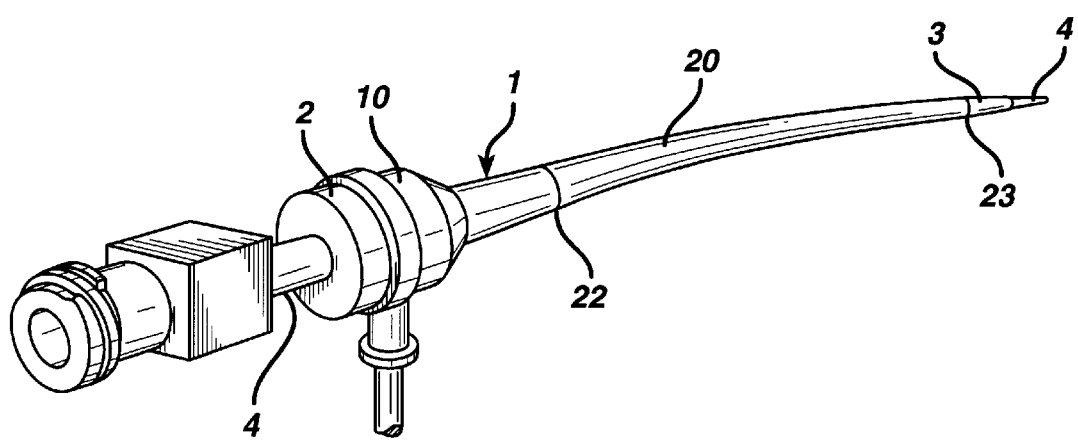
FIG. 1 is a perspective view of a catheter introducer in accordance with the present invention, shown with a vessel dilator and ready for insertion into the vessel of a patient.
Figure 2:
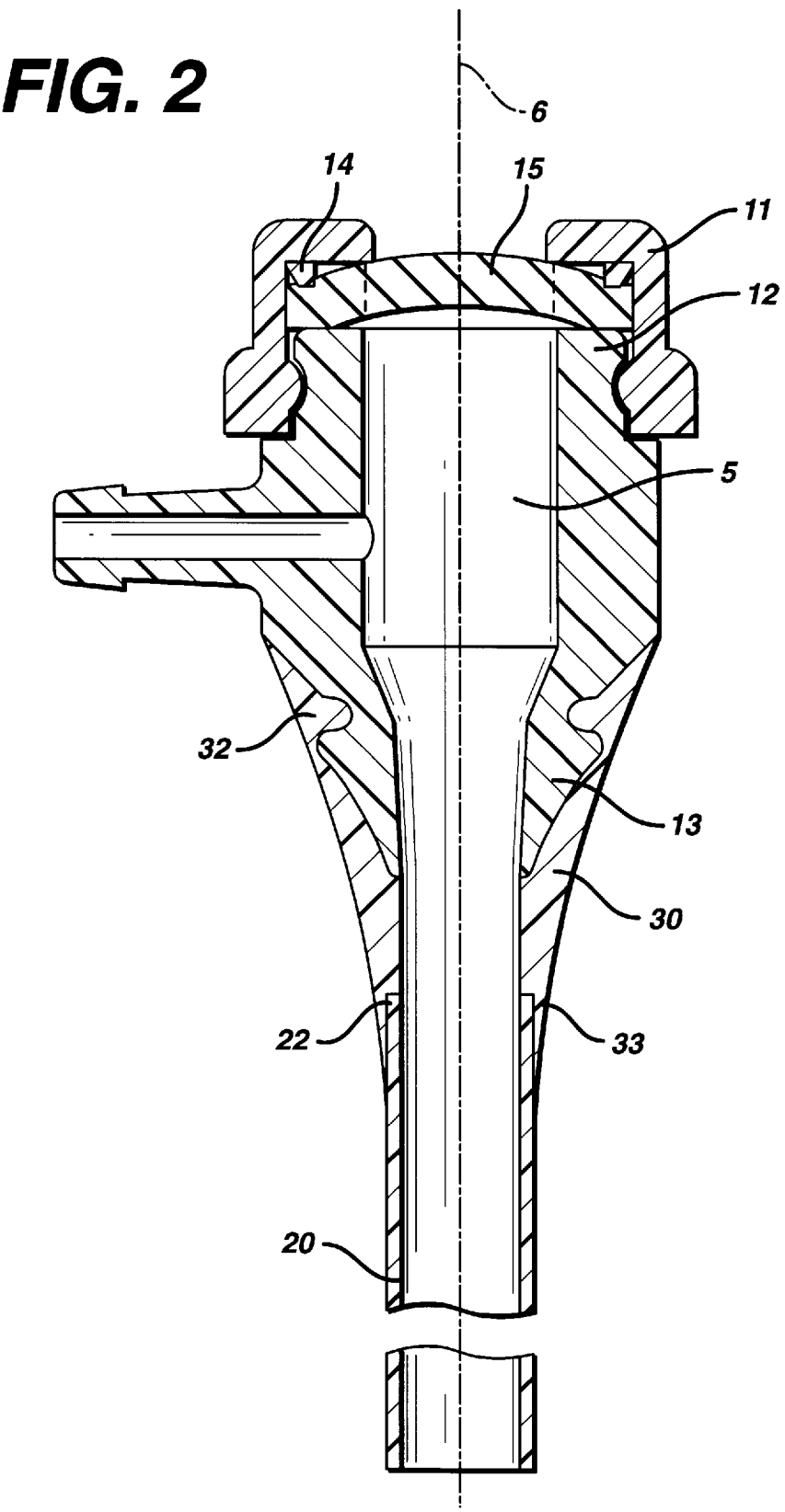
FIG. 2 is a cross-sectional view of the proximal end of the catheter sheath introducer of the present invention taken parallel to its longitudinal axis.

Referring to the drawings wherein like numerals indicate the same elements throughout the views, there is shown in FIGS. 1 and 2 a catheter, or catheter sheath introducer, 1 in accordance with the present invention. Catheter 1 is designed to be inserted into the vessel of a patient and serve as an entrance site for other catheters, guidewires or the like. Catheter 1 includes a proximal end 2 having a rigid housing or hub 10 attached thereto. Housing 10 has a proximal end 12 and a distal end 13. Catheter 1 also has a distal end 3 having a flexible tube or cannula 20. Tube 20 has a proximal end 22 and a distal end 23. Preferably distal end 23 of tube 20 has two portions wherein the outside diameter is tapered, preferably at different angles. This design is set forth in U.S. Pat. No. 5,417,665 issued to De La Mata et al., which is hereby incorporated herein by reference. Catheter 1 further includes a lumen 5 extending through the catheter parallel to its longitudinal axis 6. The housing 10 has an annular valve 15 at its proximal end 12 for access to the lumen 5 of catheter 1. A dilator 4 passes into the valve, through the lumen and out through the distal end 23 of tube 20. The dilator 4 is tapered at its end and helps introduce catheter 1 into the vessel of the patient. After the distal end 3 of the catheter 1 is inserted into the vessel of a patient, the dilator stylet is removed.

As seen from FIG. 2, the housing 10 has an end cap 11, attached to its proximal end, and annular valve 15. Valve 15 preferably comprises an elastomer having 4–6 slits extending through the partition at an angle. The elastomer preferably has from about 5 to about 20 percent by weight of a lubricity enhancing additive such as bismuth oxychloride, polytetrafluoroethylene, titanium dioxide, graphite, polyethylene wax or the like. The end cap preferably has a compression ring 14 having a diameter less than or equal to the diameter of the partition. This causes the partition to bow upwardly which enhances the sealing of the slits. A preferred description of the valve is given in pending U.S. Pat. No. 5,453,095 and U.S. patent application Ser. No. 08/275,828 "Catheter Hemostasis Valve" filed on Jul. 15, 1994, both of which are hereby incorporated herein by reference.

In accordance with the present invention, catheter 1 includes a resilient transition member 30, intermediate and separating housing 10 and tube 20 so that there is no direct contact between the two. Member 30 has a proximal end 32 attached to distal end 13 of housing 10, and a distal end 33 attached to the proximal end 22 of tubing 20. The transition member 30 is made from a material having greater flexibility and preferably a lower durometer than the material the tube is made from. Typically the tube 20 is made from a material such as nylon wherein the tube can be bent at an angle from about 20° to about 40° before it kinks. Member 30 is preferably made from a more flexible material such as polyurethane, low durometer nylon, low density polyethylene, soft pebax or any suitable elastomeric material. One such material is polyurethane-80A, wherein the member can be bent at an angle from about 30° to about 110° before it kinks. The transition member 30 preferably has the necessary resiliency such that it will deform back to its original position after the catheter is bent.

Preferably, the plastic housing 10 is molded and the tube 20 is extruded separately. Thereafter, the transition member could be molded onto the housing and the tube. The transition member would melt onto the tube and housing. This provides for a good seal between all three pieces. However, as appreciated by those skilled in art, other manufacturing methods and materials could be used to construct catheter 1.

Preferably, as shown in FIG. 2, the transition member tapers from a large diameter, adjacent the housing, down to a smaller diameter, adjacent the tube. This tapering provides for a smooth transition between the hub and the tube and helps prevent kinking. At least a portion of transition member 30 preferably has an outside diameter which is substantially larger than the diameter of the lumen 5 and larger than the outside diameter of tube 20. It is preferable that at least a portion of the transition member have an outside diameter which is from about 50% to about 400% larger than the diameter of the lumen.

The design of the catheter of the present invention, allows the physician to bend the catheter, after inserting it into the patient, without significantly reducing the inside diameter of the lumen 5. Instead of a sharp kink point, the catheter will bend smoothly along the length of the transition member. Because the transition member 30 is more flexible than the tube 20 it creates a point of weakness in the catheter. That is when the physician bends the catheter, it will bend at the weakest point, which is along the transition member. Furthermore, because the outside diameter of the transition member is larger than the lumen, there is preferably enough material to compress and stretch without significantly reducing the diameter or cross-sectional area of the lumen along the transition member where it bends. The transition member allows for a smooth continuous bend over the transition member, rather than a sharp kink or bend point exhibited by prior art devices at the connection point between the tube and housing.

Although particular embodiments of the present invention have been shown and described, modification may be made to the catheter without departing from the spirit and scope of the present invention. The terms used in describing the invention are used in their descriptive sense and not as terms of limitations.

That which is claimed is:

1. A catheter having a distal end for insertion into a body vessel, a proximal end for remaining external of the body vessel and a lumen extending therethrough, said catheter comprising:
   a) a rigid housing at said proximal end, said housing having a distal and proximal end, said housing having an annular valve at its proximal end for access to said lumen;
   b) a flexible tube for insertion into the patient, said tube having a predetermined outside diameter, a proximal end and a distal end;
   c) a resilient transition member intermediate and separating said housing and said tube, said member having a proximal end attached to said distal end of said housing and a distal end attached to said proximal end of said tubing, said transition member is made from a material having greater flexibility and a lower durometer than a material said tube is made from; and
   d) said transition member having an outside diameter which tapers from a large diameter at its proximal end to a smaller diameter at its distal end.

2. The catheter according to claim 1 wherein said transition member is made from a material selected from the group comprising:
   polyurethane, low durometer nylon, low density polyethylene, soft pebax.

3. The catheter according to claim 1 wherein at least a portion of said transition member has an outside diameter which ranges from about 50% to about 400% larger than the diameter of said lumen.

4. A catheter having a distal end for insertion into a body vessel, a proximal end for remaining external of the body vessel and a lumen extending therethrough, said catheter comprising:
   a. a rigid housing at said proximal end, said housing having a distal and proximal end, said housing having an annular valve at its proximal end for access to said lumen;
   b. a flexible tube for insertion into the patient, said tube having a predetermined outside diameter, a proximal end and a distal end; and
   c. a resilient transition member intermediate and separating said housing and said tube, said member having a proximal end attached to said distal end of said housing and a distal end attached to said proximal end of said tubing, said transition member is made from a material having greater flexibility and a lower durometer than a material that said tube is made from, and wherein at least a portion of said transition member has an outside diameter which ranges from about 50% to about 400% larger than the and diameter of said lumen.

5. The catheter according to claim 4 wherein said outside diameter of said transition member is greater than the outside diameter of said tube.

6. The catheter according to claim 4 wherein said transition member is made from a material selected from the group comprising:
   polyurethane, low durometer nylon, low density polyethylene, soft pebax.

7. The catheter according to claim 4 wherein the outside diameter of said transition member tapers from a large diameter at its proximal end to a smaller diameter at its distal end.

8. A catheter having a distal end for insertion into a body vessel, a proximal end for remaining external of the body vessel and a lumen extending therethrough, said catheter comprising:
   a. a rigid housing at said proximal end, said housing having a distal and proximal end, said housing having an annular valve at its proximal end for access to said lumen;
   b. a flexible tube for insertion into the patient, said tube having a predetermined outside diameter, a proximal end and a distal end; and
   c. a resilient transition member intermediate and separating said housing and said tube, said member having a proximal end attached to said distal end of said housing and a distal end attached to said proximal end of said tubing, said transition member tapering from a large outside diameter at its proximal end to a smaller outside diameter at its distal end, said transition member is made from a material having greater flexibility and a lower durometer than a material that said tube is made from, and wherein at least a portion of said transition member has an outside diameter which ranges from about 50% to about 400% larger than the diameter of said lumen.

9. The catheter according to claim 8 wherein said transition member is made from a material selected from the group comprising:

polyurethane, low durometer nylon, low density polyethylene, soft pebax.

* * * * *